United States Patent
Michels et al.

(10) Patent No.: US 7,729,783 B2
(45) Date of Patent: Jun. 1, 2010

(54) APPARATUS AND METHODS FOR VACUUM- AND MECHANICALLY-ASSISTED FIXATION OF MEDICAL ELECTRICAL LEADS

(75) Inventors: Koen Michels, Maastricht (NL); Fredric W. Lindemans, Sittard (NL); Jean-Luc Jansens, Merchtem (BE)

(73) Assignee: Medtronic, Inc., Minneapolis, MN (US)

( * ) Notice: Subject to any disclaimer, the term of this patent is extended or adjusted under 35 U.S.C. 154(b) by 850 days.

(21) Appl. No.: 11/380,228

(22) Filed: Apr. 26, 2006

(65) Prior Publication Data

US 2007/0255375 A1    Nov. 1, 2007

(51) Int. Cl.
*A61N 1/05* (2006.01)

(52) U.S. Cl. ............... 607/130; 607/119; 607/126; 607/129

(58) Field of Classification Search .......... 607/116, 607/119, 122, 129, 130
See application file for complete search history.

(56) References Cited

U.S. PATENT DOCUMENTS

| | | | |
|---|---|---|---|
| 5,249,574 A * | 10/1993 | Bush et al. ........ | 607/9 |
| 5,336,252 A | 8/1994 | Cohen | |
| 6,613,062 B1 | 9/2003 | Leckrone et al. | |
| 6,666,844 B1 * | 12/2003 | Igo et al. ........ | 604/115 |
| 2003/0069577 A1 * | 4/2003 | Vaska et al. ........ | 606/41 |
| 2003/0167056 A1 * | 9/2003 | Jahns et al. ........ | 606/41 |
| 2003/0212446 A1 | 11/2003 | Kaplan et al. | |
| 2004/0138527 A1 | 7/2004 | Bonner et al. | |
| 2004/0176830 A1 * | 9/2004 | Fang ........ | 607/129 |
| 2004/0204750 A1 * | 10/2004 | Dinh ........ | 623/1.15 |
| 2006/0161238 A1 * | 7/2006 | Hall ........ | 607/129 |

FOREIGN PATENT DOCUMENTS

| | | |
|---|---|---|
| WO | WO9640368 | 12/1996 |
| WO | WO2005113061 | 12/2005 |

* cited by examiner

*Primary Examiner*—Carl H Layno
*Assistant Examiner*—Jennifer Stewart
(74) *Attorney, Agent, or Firm*—Stephen W. Bauer

(57) ABSTRACT

A method and apparatus for providing positive fixation of medical components to a portion of pericardial tissue via both vacuum- and/or mechanically-assisted means. A source of vacuum couples via a lumen to a recessed portion of a body structure deployed into the pericardial space. The recessed portion is adapted to form a seal around its periphery with adjacent pericardial tissue so that when the recessed portion is evacuated, the tissue is drawn into the recessed portion. Then, a sharpened instrument, such as a stylet, is deployed through the lumen and pierces the tissue, thus anchoring the body structure. A source of fluid may also be included for delivery to the pericardial space (e.g., contrast media; saline solution; biological, genetic and pharmaceutical substances and the like).

12 Claims, 5 Drawing Sheets

APPARATUS AND METHODS FOR VACUUM- AND MECHANICALLY-ASSISTED FIXATION OF MEDICAL ELECTRICAL LEADS

CROSS REFERENCE TO RELATED APPLICATIONS AND PATENT

The present disclosure relates to the following co-pending applications; namely, U.S. application Ser. No. 11/000,539 by Morris et al. captioned, "METHODS AND SYSTEMS FOR ACCESSING THE PERICARDIAL SPACE," U.S. application Ser. No. 11/000,538 by Sigg et al. captioned, "METHODS AND SYSTEMS FOR PROVIDING THERAPIES INTO THE PERICARDIAL SPACE," and U.S. application Ser. No. 11/380,234, filed Apr. 26, 2006 entitled, "PERICARDIUM FIXATION CONCEPTS OF EPICARDIUM PACING LEADS AND TOOLS," filed on common day herewith, the contents of which are incorporated herein by reference. In addition, this disclosure incorporates the contents of U.S. Pat. No. 6,613,062 to Leckrone et al. captioned, "METHOD AND APPARATUS FOR PROVIDING INTRA-PERICARDIAL ACCESS," which issued 2 Sep. 2003.

BACKGROUND

Certain embodiments in the present disclosure pertain to medical component delivery and more particularly to tools for delivering active medical components for chronic attachment within the pericardial space.

In certain instances, a patient suffering from bradycardia, tachyarrhythmia and/or heart failure will benefit from electrical stimulation pacing and/or defibrillation electrodes implanted on an epicardial surface of the patient's heart.

Minimally invasive methods for accessing the epicardial surface, which is enclosed within a pericardial sac, have recently been developed; these methods provide for piercing through the pericardial sac in order to access the epicardial surface; an example of one such method is described in commonly assigned U.S. Pat. No.6,837,848. These methods may be used by way of a mini-thoracotomy or in conjunction with a trocar, canula or catheter that has been passed, via a percutaneous incision, through an interstitial space between the patient's ribs or by a sub-xiphoid approach; those skilled in the art are familiar with these techniques.

Once access to the epicardial surface is established, the implanting physician may desire to implant into the pericardial space a medical electrical lead, including an appropriate electrode configuration and/or one or more physiologic sensors suited to the patient's need. The physician will almost always need to maneuver the electrode-bearing portion of the lead within the space in order to implant the components at an appropriate location and in a way to provide effective and stable chronic cardiac therapy and/or monitoring of various physiologic parameters.

SUMMARY

The present invention pertains to methods and apparatus for providing positive fixation of medical components to a portion of pericardial tissue via both vacuum-and mechanically-assisted means. According to the invention, a source of vacuum couples via a lumen to a recessed portion of a body structure deployed into the pericardial space. The recessed portion is adapted to form a seal around its periphery with adjacent pericardial tissue so that when the recessed portion is evacuated, the tissue is drawn into the recessed portion. Then, a sharpened instrument, such as a stylet, is deployed through the lumen and pierces the tissue, thus anchoring the body structure. In related embodiments in lieu of or in addition to the application of vacuum to the recessed portion, a source fluid can be configured so that diverse fluids can be delivered to the pericardial space (e.g., contrast media; saline solution; biological, genetic and pharmaceutical substances and the like).

Diverse medical components can thus be safely and reliably chronically deployed into the pericardial space, including without limitation, cardiac sensing/pacing, defibrillation and/or cardioversion electrodes, mechanical and/or metabolic sensors and the like. More than one body structure can be linked to a single medical electrical lead and the medical components can couple within and/or upon a portion of the body structure and the lead in myriad configurations.

It should be noted that, although most embodiments of the present invention are described herein in the context of epicardial sensing/pacing, cardioversion and/or defibrillation and diverse physiologic sensing applications, the invention is not so limited. Those skilled in the art will appreciate that numerous minor alterations and modifications can be implemented to provide a wide variety of cardiac therapies, diagnostics and/or monitoring capabilities. For example, while not specifically depicted herein the present invention can be used to deliver so-called paired-and coupled-pacing therapy whereby a pacing stimulus delivered immediately following the end of the refractory period causes an extra-systole for subsequent cardiac cycles. Also, so-called non-excitatory stimulation can be delivered in which electrical stimulation is delivered during the refractory period (absolute and/or relative) to provide contractility benefits and the like.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention.

As is known to those in the art of cardiac surgery, electrophysiology, and/or interventional cardiology, an exemplary delivery tool is used to position a medical electrode assembly and/or a physiologic sensor which couples to a portion of a medical electrical lead for deployment of the assembly and/or sensor to an epicardial surface of a heart. According to some embodiments of the present invention, the assembly and/or sensor include one or more pacing or defibrillation electrodes and a physiologic sensor (e.g., a metabolic sensor, a mechanical sensor such as an accelerometer or the like, a pressure sensor, etc.). In addition, more than one electrode and/or sensor assembly can be deployed on a single medical electrical lead or dedicated electrode units and dedicated sensor units can be deployed individually or coupled to a common lead or several dedicated medical electrical leads. Known electrical multiplexing techniques can be used to provide and receive signals from the units.

A proximal end of a medical electrical lead operatively couples the unit or units to pacing, sensing, and/or cardioversion/defibrillation circuitry, in the case of electrodes, and to appropriate signal processing circuitry, in the event that sensors are deployed.

A variety of deployment techniques and delivery tools can be used in conjunction with the apparatus of the present invention that would typically include an elongated shaft having a distal portion coupled to a shaft portion. During deployment the distal portion is inserted between an epicardial surface of the heart and a pericardial sac surrounding the heart through a pericardial incision. According to certain embodiments of the present invention, the shape of the distal portion can be adjusted to facilitate insertion of the assembly and/or sensor between the pericardium and epicardium.

Figure 1:
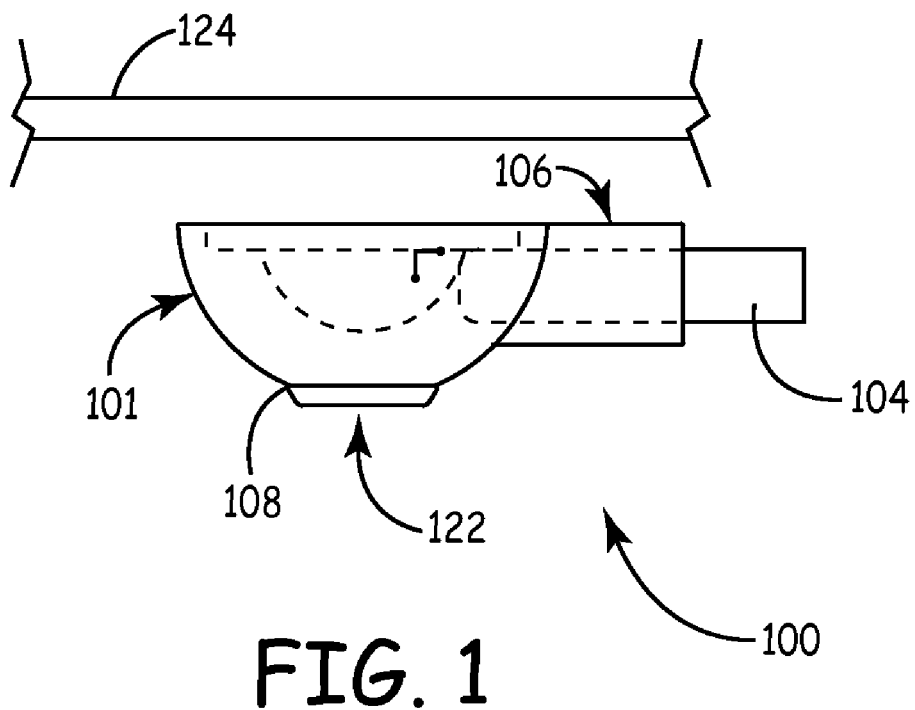
FIG. 1 is an elevational schematic view of an active pericardial fixation apparatus according to the present invention depicted spaced from an adjacent portion of pericardial tissue.

FIG. 1 is an elevational schematic view of an active pericardial fixation apparatus 100 according to the present invention depicted spaced on a first side 106 from an adjacent portion of pericardial tissue 124. The apparatus comprises a body structure 101 and at least one physiologic parameter-sensing and/or cardiac rhythm management component 122. Thus, although only a single component 122 disposed on a second side 108 of body 101 is depicted in FIG. 1 more than one component 122 can be operably deployed with an active fixation apparatus 100 according to the invention. The body structure 101 of the apparatus 100 mechanically and electrically couple to a portion of a medical electrical lead 104. The lead 104 thus includes at least one elongated conductor for transferring electrical power and signals to and from component 122 to remotely located medical device circuitry (e.g., pulse generator, sensor signal processing, defibrillation and cardioversion circuitry and the like). In some forms of the invention the lead 104 includes a hollow lumen and is optionally adapted to receive a stylet as will be described further hereinbelow.

A component 122 can couple within and/or upon the body 101 and the lead 104. For instance a pair of closely spaced-apart electrodes can be electrically coupled in a bi-polar pacing configuration and at least one sensor, such as an accelerometer can be coupled within the body 101. Those of skill in the art will recognize that myriad configurations can be implemented. In addition, more than one apparatus 100 can be deployed within the pericardial space of a heart. Each apparatus 100 can be coupled to a dedicated medical electrical lead 104 or can be coupled to a common lead 104.

According to some embodiments of the invention body structure 101 and/or lead 104 can be comprised of a biocompatible polymer as well as other known biocompatible materials. Regarding fabrication techniques, body structure 101 and lead 104 can be individually fabricated or can form an integrated unit. The body structure and/or lead 104 can be injection molded from a polymer having a relatively high modulus of elasticity, yet being sufficiently elastic and not prone to brittle fracture, for example 75D durometer polyurethane or high density polyethylene or polyamide. Alternately, one or both can be insert molded or formed by molding or an extrusion process. According to some embodiments, portions can be wholly or partially formed from a metal having suitable elastic and elastomeric properties, examples of which include, but are not limited to, titanium alloys, Ni—Ti superelastic alloys and stainless steel and the like. Other suitable materials can also be used as known in the art.

Figure 2:
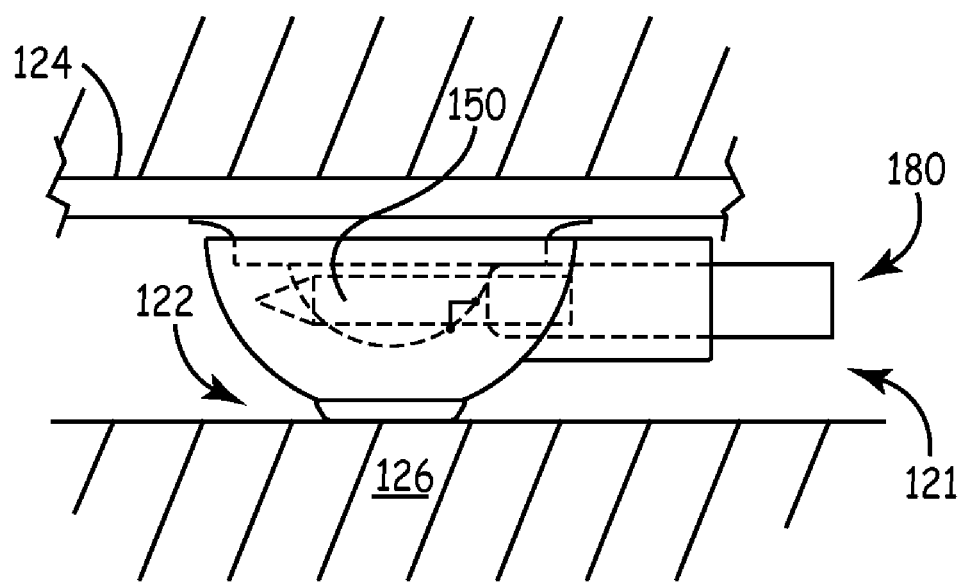
FIG. 2 is an elevational schematic view of an active pericardial fixation apparatus according to the present invention depicted in contact with an adjacent portion of pericardial tissue.

FIG. 2 is an elevational schematic view of an active pericardial fixation apparatus 100 according to the present invention depicted within the pericardial space 121 of a heart and in contact on the first side (106) with an adjacent portion of pericardial tissue 124. The body structure 101 contacts epicardial tissue 126 on the second side (108). Once situated as depicted in FIG. 2, the component 122 of body structure 101 is disposed in electrical communication with excitable myocardial tissue of the epicardium 126 and can sense and/or deliver pacing therapy as well as provide high voltage therapies (e.g., cardioversion, defibrillation). As mentioned with respect to FIG. 1, in addition to or in lieu of such a configuration, one or more sensors can be coupled to the body 101 and/or the lead 104. As depicted in FIG. 2 the lead 104 includes a lumen 180 adapted to receive a stylet of other elongated and relatively flexible member 150. The member 150 can be manually advanced and retracted within the lumen 180 by manipulating a proximal portion thereof as is known in the art. The member 150 can be one or more radio-opaque markers or the like (e.g., 152 in FIG. 5) so that the location of the member 150 can be visualized with, for example, fluoroscopy equipment. The member 150 can optionally include a lumen or passageway from a proximal end portion to a distal end portion thereof adapted to dispense diverse fluids. Thus either the lead 104 and/or the member 150 can be employed to dispense fluid materials (e.g., contrast media, saline solution, biological, genetic, pharmaceutical, as well as other therapeutic and/or palliative substances).

Figure 3:
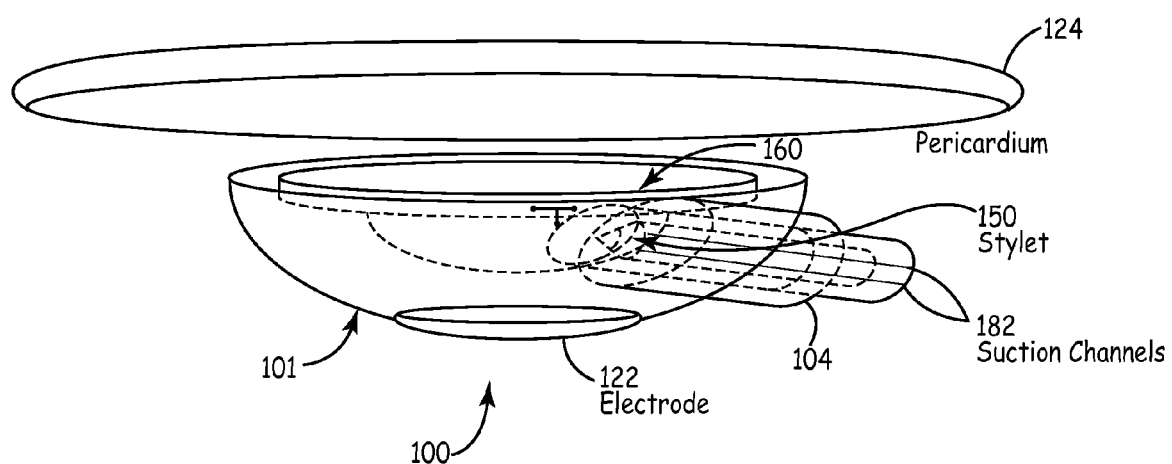
FIG. 3 is an enlarged perspective view depicting interior components in an exemplary configuration of one embodiment of an active pericardial fixation apparatus according to the invention disposed in spaced relationship relative to adjacent pericardial tissue.

FIG. 3 is an enlarged perspective view depicting interior components in an exemplary configuration of one embodiment of an active pericardial fixation apparatus 100 according to the invention disposed in spaced relationship relative to adjacent pericardial tissue 124 (schematically represented by a disk-shaped object). The body 101 of the apparatus 100 includes a recessed chamber 160 fluidly coupled to a lumen (180 in FIG. 2) of the lead 104. The lumen is also adapted to receive a stylet member 150 and to fluidly couple to a remote source of vacuum (160' in FIG. 5). Thus, when the recessed chamber 160 is evacuated by the remote source of vacuum a suction force is generated that tends to draw adjacent pericardial tissue 124 into the chamber 160. The stylet 150 preferably includes a sharpened distal end or tip so that once the pericardial tissue 124 is drawn into the chamber 160, the stylet is advanced thus piercing the tissue 124 and actively fixing the apparatus 100 into place within the pericardial space.

As depicted in FIG. 3 a plurality of channels 182 are optionally formed within the lumen (although a single optional channel could be employed). The optional channels 182 provide at least two functional features to the operation of apparatus 100; first of all, they allow the vacuum source 160' to continue to evacuate the chamber 160 when the stylet is being advanced, and second, they promote ease of movement to the stylet along its oftentimes serpentine path.

Figure 4:
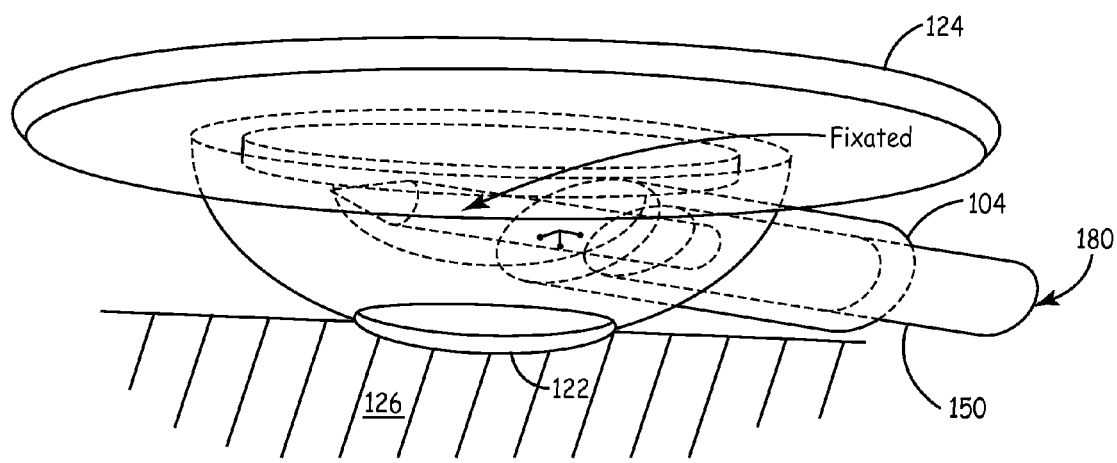
FIG. 4 is an enlarged perspective view depicting interior components in an exemplary configuration of one embodiment of an active pericardial fixation apparatus according to the invention located in contact with pericardial tissue on a first side and in contact with epicardial tissue on a second side.

FIG. 4 is an enlarged perspective view depicting interior components in an exemplary configuration of one embodiment of an active pericardial fixation apparatus 100 according to the invention fixated in contact with pericardial tissue 124 on a first side (106 in FIG. 1) and in contact with epicardial tissue 126 on a second side (108 in FIG. 1). As just described with reference to FIG. 3, the apparatus 100 is initially fixed due to a remote source of vacuum and subsequently is mechanically fixed with the stylet member 150. FIG. 4 is intended to also show that the stylet member 150 can itself comprise a hollow member having a lumen 180. In this form of the invention the channel features (182 in FIG. 3) are not required to allow the source of vacuum to evacuate the chamber 160. As long as an adequately-sized aperture is disposed on or near the distal tip of the stylet member 150 evacuation of the chamber 160 can take place.

Figure 5:
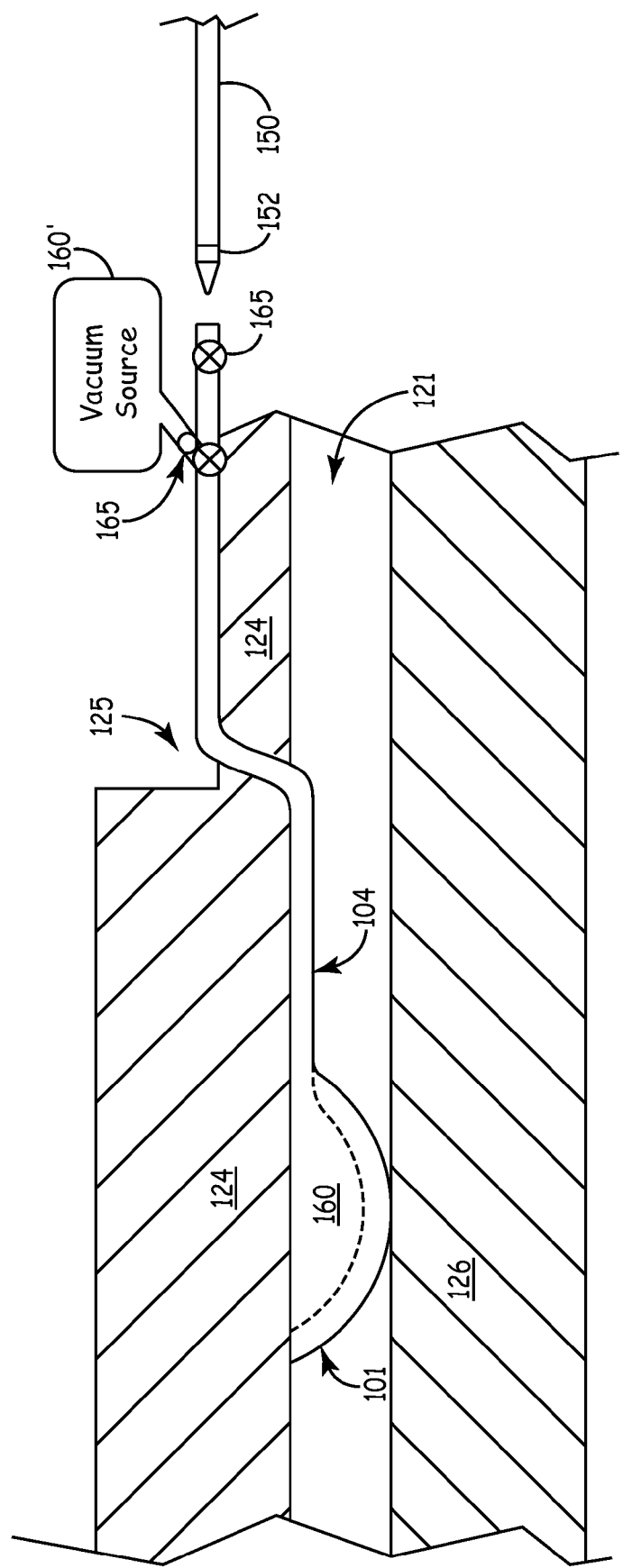
FIG. 5 schematically depicts an embodiment of an apparatus according to the invention disposed within the pericardial space of a heart and fluidly coupled to a source of vacuum during an implantation procedure.

FIG. 5 schematically depicts an embodiment wherein a body structure 101 of an apparatus according to the invention is disposed within the pericardial space 121 of a heart and fluidly coupled to a source of vacuum 160' during an implantation procedure. Lead 104 is shown passing through the pericardium 124 at 125. One or more valves 165 can be disposed intermediate the vacuum source 160' and the lead 104 to allow evacuation of the chamber 160 during implantation. As mentioned, in the event that a hollow stylet 150 is implemented, the vacuum source 160' could simply be coupled directly to a proximal portion of the hollow stylet 150. Also, as previously mentioned in addition to or in lieu of the vacuum source 160' other or different fluid dispensing apparatus could be coupled to the lead 104 and/or the hollow stylet 150. When activated such apparatus would provide one or more fluids to the chamber 160 and thus to one of the pericardial space 121 and the adjacent, pierced pericardial tissue 124. As noted above, the stylet member 150 can optionally include one or more visualization markers 152 to assist deployment and confirm the location of the member 150 during implantation procedures.

The configuration depicted in FIG. 5 can be acutely implement to relieve excess fluid build-up in the pericardial space (i.e., tamponade). For example, the source of vacuum can be employed to help aspirate fluid from the pericardial space 121. Alternately, the configuration can be implemented to provide palliative substances to the pericardial space 121, for example, in an effort to relieve symptoms of an acute episode of pericarditis.

Figure 6:
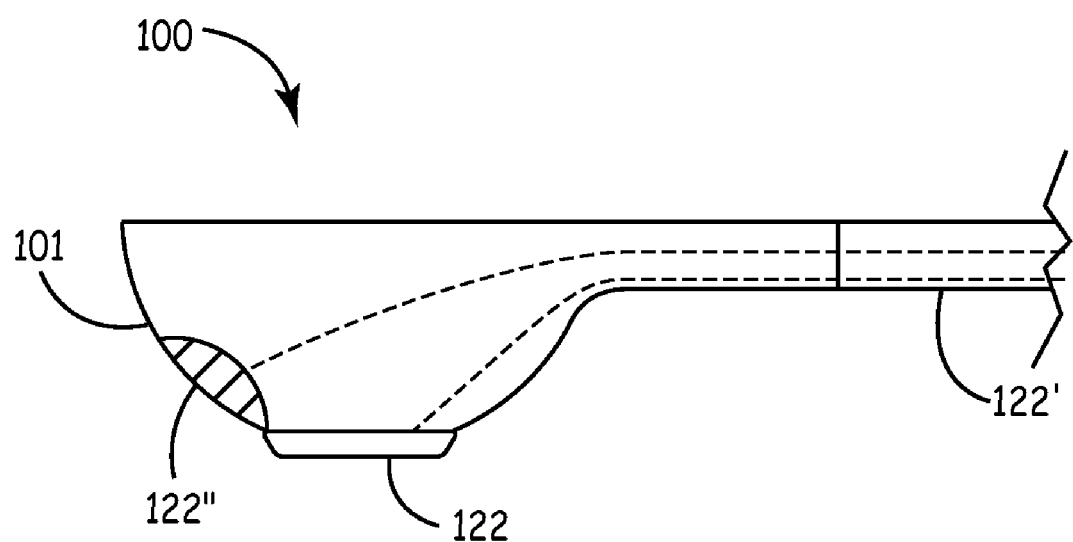
FIG. 6 schematically depicts an embodiment of an active pericardial fixation apparatus according to the present invention that includes multiple implantable physiologic sensors and/or electrodes.

FIG. 6 schematically depicts an embodiment of an active pericardial fixation apparatus 100 according to the present invention that includes multiple implantable physiologic sensors and/or electrodes 122,122',122" disposed within and/or upon a portion of body 101 and lead 104.

In the foregoing detailed description, the invention has been described with reference to specific embodiments. However, it may be appreciated that various modifications and changes can be made without departing from the scope of the invention as set forth in the appended claims. For example, the lumen described as part of a medical electrical lead can be independently coupled to the recessed portion that provides a suction-retaining force to the body structure. In this form of the invention, the independent lumen structure can be closed via a valve structure or simply compressed or pinched to a closed state and the remaining portions removed so that the vacuum or suction-retaining force continues to fixate the body structure. One aspect of this derivative form of the invention is that a stylet or other mechanical means for piercing the pericardium becomes an optional feature, as the suction-retaining forces alone are adequate for retaining the body structure.

The invention claimed is:

1. An apparatus for securing an implantable medical device (IMD) within the pericardial space via vacuum-and/or mechanically-assisted techniques, comprising:
   a body structure comprised of biocompatible material, said body structure having an epicardium-contacting side and an opposing pericardial sac-contacting side, wherein said body structure includes a recessed portion on the pericardial sac-contacting side;
   an elongated medical electrical lead mechanically and electrically coupled to said body structure and fluidly coupled to the recessed portion, wherein the fluid coupling results from a lumen extending from a proximal end portion of the lead to said recessed portion;
   an electrode mounted on the epicardium contacting side of the body structure;
   a vacuum source coupled to the lumen and configured to evacuate the recessed portion; and
   a deployable stylet disposed within the lumen and configured to pierce a portion of pericardial tissue when the vacuum source evacuates the recessed portion.

2. An apparatus according to claim 1, wherein the electrode comprises a cardiac pacing electrode.

3. An apparatus according to claim 1, further comprising a valve operatively coupled to the lumen and adapted to control the amount of suction provided by the vacuum source.

4. An apparatus according to claim 1, further comprising a radio-opaque marker coupled to the deployable stylet.

5. An apparatus according to claim 4, wherein the radio-opaque marker is disposed near a distal end of the deployable stylet.

6. An apparatus according to claim 4, wherein the deployable stylet includes a longitudinal lumen.

7. An apparatus according to claim 6, further comprising a source of fluid coupled to the lumen of the deployable stylet.

8. An apparatus according to claim 7, wherein the source of fluid comprises one of: a source of contrast media, a source of saline solution, a source of biological material, a source of genetic material, a source of pharmaceutical material.

9. An apparatus according to claim 1, wherein the body structure is comprised of medical grade polyurethane.

10. An apparatus according to claim 9, wherein the recessed portion comprises a substantially hemispherical portion.

11. An apparatus according to claim 10, wherein the body structure comprises a substantially dome-shaped structure.

12. An apparatus according to claim 11, wherein an outer curved portion of the dome-shaped structure is configured to contact epicardial tissue and the recessed portion is disposed on the side opposing the outer curved portion.

* * * * *